United States Patent
Zamorano Mendieta et al.

(10) Patent No.: US 11,424,022 B2
(45) Date of Patent: Aug. 23, 2022

(54) METHOD FOR PROCESSING BRAIN IMAGES

(71) Applicant: Universidad del Desarrollo, Las Condes (CL)

(72) Inventors: Francisco Zamorano Mendieta, Las Condes (CL); Pablo Billeke Bobadilla, Las Condes (CL)

(73) Assignee: Universidad del Desarrollo, Las Condes (CL)

( * ) Notice: Subject to any disclaimer, the term of this patent is extended or adjusted under 35 U.S.C. 154(b) by 0 days.

(21) Appl. No.: 17/058,788

(22) PCT Filed: Mar. 27, 2019

(86) PCT No.: PCT/CL2019/050019
§ 371 (c)(1),
(2) Date: Nov. 25, 2020

(87) PCT Pub. No.: WO2019/227245
PCT Pub. Date: Dec. 5, 2019

(65) Prior Publication Data
US 2021/0202074 A1      Jul. 1, 2021

(30) Foreign Application Priority Data

May 29, 2018   (CL) ................................ 2018001428

(51) Int. Cl.
*G06K 9/00*      (2022.01)
*G16H 30/40*    (2018.01)
(Continued)

(52) U.S. Cl.
CPC ............. *G16H 30/40* (2018.01); *G06T 7/149* (2017.01); *G06T 7/37* (2017.01);
(Continued)

(58) Field of Classification Search
CPC ........... G16H 30/40; G06T 7/149; G06T 7/37; G06T 2207/10088; G06T 2207/10104;
(Continued)

(56) References Cited

U.S. PATENT DOCUMENTS

2005/0244036 A1\* 11/2005 Rusinek .................. A61B 5/05
                                                                  382/120
2006/0025673 A1\*  2/2006 De Leon ............... G06T 7/0012
                                                                  600/410
(Continued)

FOREIGN PATENT DOCUMENTS

AU        2012350363 B2      1/2018

OTHER PUBLICATIONS

International Search Report and Written Opinion dated Jul. 3, 2019 for PCT Application No. PCT/CL2019/050019, 18 pages.
(Continued)

*Primary Examiner* — Atiba O Fitzpatrick
(74) *Attorney, Agent, or Firm* — Benesch, Friedlander, Coplan & Aronoff LLP

(57) ABSTRACT

The present invention relates to a novel methodology for the field of brain images from Positron Emission Tomography (PET), likewise applicable to brain images from Single-Photon Emission Computer Tomography (SPECT) or another technique that makes it possible to generate images of brain metabolism, function or blood flow. This methodology arises from the need to improve the medical diagnosis of neurological disorders and from the need for objective, unbiased quantification of brain metabolism. The method is based on the spatial symmetry of the metabolism of the healthy human brain. Under this assumption, the entire healthy brain metabolism can be deduced from the metabolism of a single hemisphere of the brain.

11 Claims, 2 Drawing Sheets

(51) Int. Cl.
*G06T 7/149* (2017.01)
*G06T 7/37* (2017.01)

(52) U.S. Cl.
CPC ............ *G06T 2207/10088* (2013.01); *G06T 2207/10104* (2013.01); *G06T 2207/10108* (2013.01); *G06T 2207/30016* (2013.01); *G06T 2207/30096* (2013.01)

(58) Field of Classification Search
CPC . G06T 2207/10108; G06T 2207/30016; G06T 2207/30096
See application file for complete search history.

(56) References Cited

U.S. PATENT DOCUMENTS

2010/0152577 A1* 6/2010 Young .................... A61B 5/055
600/431
2014/0307936 A1* 10/2014 Dore ..................... G06T 7/0016
382/131
2017/0083780 A1 3/2017 Akamatsu et al.
2018/0103921 A1* 4/2018 Huang ................... A61B 6/037

OTHER PUBLICATIONS

Zanzonico, Pat B., et al., "Introduction to Clinical and Laboratory (Small-Animal) Image Registration and Fusion", Proceedings of the 28th IEEE EMBS Annual International Conference, 2006, pp. 1580-1583.
Jan, Meei-Ling, et al., "A Three-Dimensional Registration Method for Automated Fusion of Micro PET-CT-SPECT Whole-Body Images", IEEE Transactions on Medical Imaging, vol. 24, No. 7, Jul. 2005, pp. 886-893.

* cited by examiner

METHOD FOR PROCESSING BRAIN IMAGES

SCOPE OF APPLICATION

The present invention relates to the creation of a database of brain images obtained by Positron Emission Tomography (PET). Specifically, a method for processing brain images from Positron Emission Tomography (PET), brain images from Single-Photon Emission Computer Tomography (SPECT) or another technique that makes it possible to generate images of brain metabolism, function and blood flow, through the spatial symmetry of the inter-hemispheric metabolism of the healthy human brain.

DESCRIPTION OF THE PRIOR ART

There is a current need to improve the medical diagnosis of neurological disorders and a need for objective, unbiased quantification of brain metabolism, using a database of age-specific PET-type brain images, to be used as healthy controls.

Currently, the market offers some solutions, such as the CortexID Suite product, GE Healthcare®, which, by introducing specific beta amyloid tracers in clinical practice, makes it possible to help with accurate and consistent quantitative results and to present the information in a personalized way designed for physicians and referring patients, providing a simple and robust review/analysis of PET and PET-CT images, by comparing images that are obtained with images of normal persons and age-layered patient groups, revealing brain functions that can be altered by disease processes. However, there is no processing of the images as taught in this invention.

The company Philips®, with its CAD4D FDG product, offers a tool for advanced, user-friendly and intuitive analysis of brain images based on voxel-wise statistical maps to detect statistically significant hypo- and hyper-metabolism regions, but does not teach image processing as taught in this invention.

Patent application GB2511052 dated 27 Aug. 2014, by Kaftan et al., entitled "A method for combining multiple image data sets into one multi-fused image," describes a method for combining multiple image data sets into a multi-fused image for display to a user which comprises aligning all the image data sets with a data set that represents corresponding anatomical data. The image data in each data set are then segmented into separate regions that represent the respective structures of interest by reference to a segmentation derived from anatomical data, and for each region a corresponding segment of image data is selected from a selected image data set. The selected segments of the image data set are combined to generate the multifunctional image of the regions.

Patent application GB2512720 dated 8 Oct. 2014, by Mathers, entitled "Methods for generating an image as a combination of two existing images, and a combined image so formed," describes generating a combined monochrome image from aligned corresponding functional (e.g. PET, SPECT) and anatomical (e.g. CT, MRI) images where the anatomical image is converted into a monochrome gradient image and combined with the functional image. The gradient image may be a vector or modulus gradient image. The functional image may be inverted. The pixel values of the gradient or functional image may be normalized by scaling or can be cropped to a scale value range before combining. Combining may be performed by multiplying the functional and gradient images in a pixel-wise fashion. The user may define a windowing operation to select a region of interest. The combined image provides a clear monochrome image that allows the user to view the functional image data without unnecessary clutter from the anatomical image.

None of the cited documents describe or teach a method for processing brain images from Positron Emission Tomography (PET), brain images from Single-Photon Emission Computer Tomography (SPECT) or another technique that makes it possible to generate images of the brain metabolism, via the generation of a database of healthy brains and the subsequent quantification of lesions based on the spatial symmetry of the inter-hemispheric metabolism of the healthy human brain.

SUMMARY OF THE INVENTION

One aim of the invention is a method for processing brain images which comprises the steps of: a) Performing a co-registration, preferably a linear co-registration with 6 degrees of freedom, or other types of co-registrations, with a transformation with no deformation, only displacement and rotation of a PET (Positron Emission Tomography) image (10) of a patient, using as reference a first volumetric MR (Magnetic Resonance) image (10) of the patient, acquired in 3D mode, generating a new PET image (20), i.e. having identical spatial properties to the volumetric MR image (10), but containing the information on the patient's brain metabolism obtained in the PET image (10); b) Calculating a first spatial transformation matrix M1, necessary for deforming the volumetric MR image (10) acquired in 3D mode, bringing it to the shape of a volumetric MR image (20); this generates a new volumetric MR image (30) which has the particularity that the inter-hemispheric groove coincides entirely with the coordinate X=0; c) Applying the matrix M1, obtained in the preceding step, to the PET image (20), generating a new PET image (30), having identical spatial properties to the volumetric MR image (30), but containing the information on the patient's brain metabolism obtained in the PET image (10); d) Determining the healthy hemisphere from the volumetric MR image (30) using the information obtained from the electroencephalographic pattern or another technique to identify the laterality of the patient's lesion, and once the healthy hemisphere has been identified, generating an image from the dimensions of the volumetric MR image (30), wherein the values on the X-axis corresponding to the healthy side are 1, and the values of the injured side are 0, and this image is referred to as region of interest ROI; e) Multiplying the volumetric MR image (30) element-wise with the image of the region of interest ROI, obtaining a new volumetric MR image (40), which corresponds only to the healthy hemisphere; copying the volumetric MR image (40) and inverting it on the X-axis, generating a mirror image of the volumetric MR image (40), referred to as volumetric MR image (50); and adding the volumetric MR image (40) element-wise with the volumetric MR image (50), generating a new volumetric MR image (60); f) Multiplying the PET image (30) element-wise with the image of the region of interest ROI, generating a new PET image (40); copying the PET image (40) and inverting it on the X-axis, generating a mirror image of the PET image (40), referred to as PET image (50); and adding the PET image (40) element-wise with the PET image (50), generating a new PET image (60); g) Calculating a second transformation matrix M2, necessary for deforming the volumetric MR image (60) to the image (MR 20); the image obtained is referred to as MR (70); h) Applying the transformation matrix M2 to the PET image (60), obtaining the PET image (70), which contains all the metabolic information of the patient's healthy hemisphere in the PET image (40), adding element-wise to the PET image (50) in the space of the volumetric MR image (20); i) Calculating a third transformation matrix M3, necessary for spatially deforming the volumetric MR image (30) to the volumetric MR image (60); and j) Applying the transformation matrix M3 to the PET image (30), obtaining the PET image (80), and applying the transformation matrix M2 to the PET image (80), obtaining a new PET image (90).

DESCRIPTION OF A PREFERRED EMBODIMENT

The present invention relates to a novel methodology for the field of brain images from Positron Emission Tomography (PET), which is likewise applicable to brain images from Single-Photon Emission Computer Tomography (SPECT) or another technique for generating images of brain metabolism, function and blood flow. This methodology arises from the need to improve the medical diagnosis of neurological disorders and from the need for objective, unbiased quantification of brain metabolism, function and blood flow.

The method is based on the spatial symmetry of the metabolism of the healthy human brain. Under this assumption, the entire healthy brain metabolism can be deduced from the metabolism of a single hemisphere of the brain.

In a considerable proportion of cases of neurological disorders, they tend to be unilateral. Through the use of the method, it is possible to reconstitute a new healthy virtual brain, based on the patient's healthy hemisphere.

This also makes it possible to create specific healthy virtual brains, which can be used as healthy controls, which makes it possible to create a database that is sorted by age or other socio-demographic variables.

Figure 1:
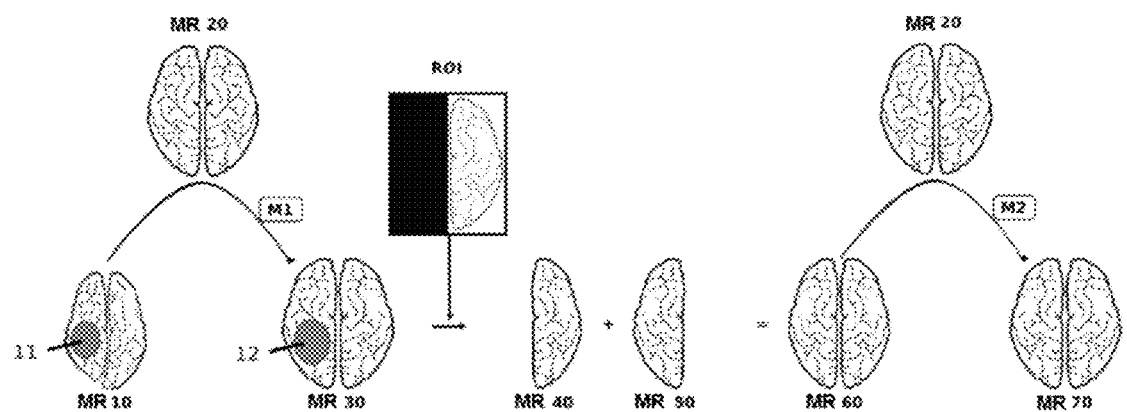
FIG. 1 describes the method for generating a structural image in the space of a template image, from the structural image of a patient's brain, acquired by Magnetic Resonance (MR).
Figure 2:
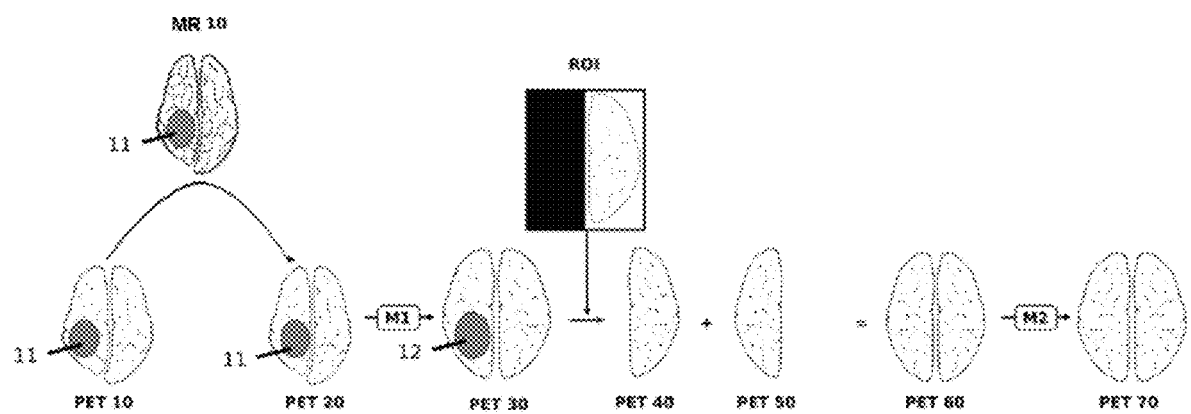
FIG. 2 describes the method for obtaining a functional image in the space of a template image, from the functional image of a patient's brain, acquired by Positron Emission Tomography or another similar technique.

The method is based on obtaining, for the brain of a patient, a volumetric MR image (10), acquired via Magnetic Resonance (MR) in 3D mode, preferably using isotropic voxels with a size smaller than or equal to 1×1×1 mm but always isotropic, as shown in FIG. 1; a PET image (10) as shown in FIG. 2, obtained by Positron Emission Tomography (PET), using radioligands such as 18FDG or others (it is also possible to use images acquired through other methodologies that capture information on brain metabolism, function or blood flow); together with this, a surface electroencephalogram or other technique for detecting the laterality of the lesion is required, since the healthy hemisphere is identified by its electrical activity as measured by electroencephalograms or different techniques for detecting physiological alterations; and an MR template image (20), which is an image acquired in 3D mode, such as an MR symmetric template, for example an MN1152 symmetric template or another symmetric template generated from MR images similar to the volumetric MR image (10) obtained from a control group paired by standardized socio-demographic characteristics with an image acquired in common 3D mode.

A first step consists in performing the co-registration, preferably a linear co-registration with 6 degrees of freedom, although other types of co-registrations can be used, i.e. a transformation with no deformation, only displacement and rotation of the PET image (10) must be carried out, using as reference the first volumetric MR image (10) acquired in 3D mode. When performing the co-registration, a new image referred to as PET (20) is generated, i.e. one having identical spatial properties to the volumetric MR image (10), but containing the information on the patient's brain metabolism obtained in the PET image (10). A lesion region (11) is shown in this first step in the volumetric MR image (10), as is shown in FIG. 1, and in the PET image (10), as is shown in FIG. 2.

The second step consists in calculating a first spatial transformation matrix M1, necessary for deforming the volumetric MR image (10) acquired in 3D mode, bringing it to the shape of a volumetric MR image (20), this process is known as Normalization; in this step a new volumetric MR image (30) is generated which has the particularity that the inter-hemispheric groove coincides entirely with the coordinate X=0. The transformation matrix resulting in the generation of the volumetric MR image (30) is referred to as matrix M1.

Figure 3:
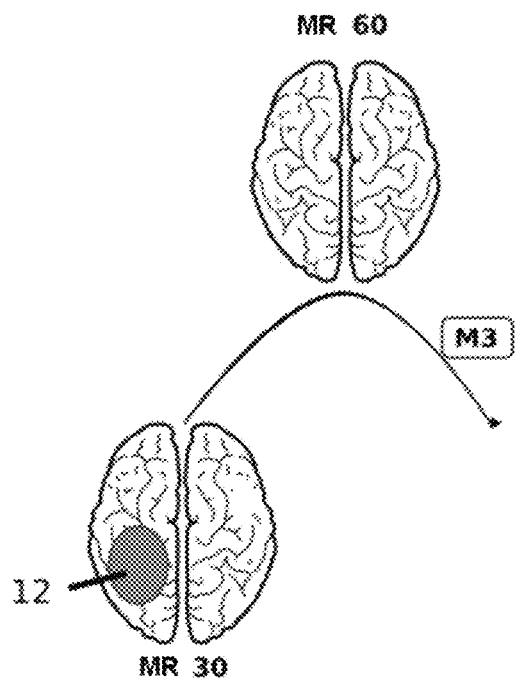
FIG. 3 describes the calculation of a third transformation matrix M3.
Figure 4:
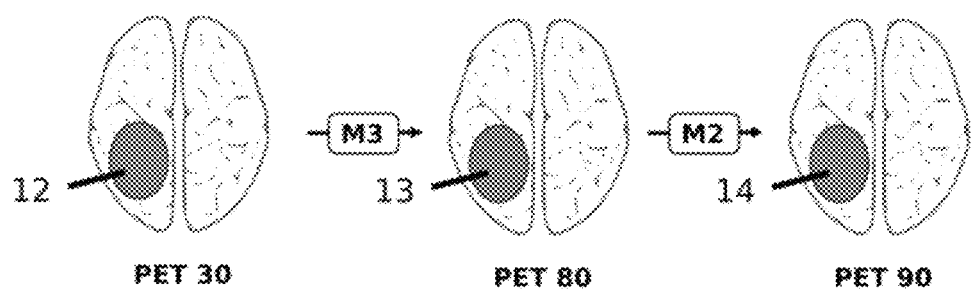
FIG. 4 describes the variation of the patient's lesion in the method.

The third step consists in applying the matrix M1, obtained in the preceding step, to the PET image (20), generating a new PET image (30), i.e. one having identical spatial properties to the volumetric MR image (30), but containing the information on the patient's brain metabolism obtained in the PET image (10). The lesion region (11), in this third step, becomes a lesion (12) for the volumetric MR image (30), as shown in FIG. 1 and FIG. 3, and in the PET image (30), as shown in FIG. 2 and FIG. 4.

The fourth step consists in determining the healthy hemisphere from the volumetric MR image (30) using the information obtained from the electroencephalographic pattern or another technique to identify the laterality of the patient's lesion, wherein this information corresponds to one of the inputs necessary for the development of the invention. Once the healthy hemisphere has been identified, an image is generated from the dimensions of the volumetric MR image (30), wherein the values on the X-axis corresponding to the healthy side are 1, and the values of the injured side are 0; this image is referred to as region of interest ROI. This matrix corresponds to the region of interest of the volumetric MR image (30).

In a fifth step, the volumetric MR image (30) is multiplied element-wise with the image of the region of interest ROI, obtaining a new volumetric MR image (40), as shown in FIG. 1, which corresponds only to the healthy hemisphere; next, the volumetric MR image (40) is copied and inverted on the X-axis, generating a mirror image of the volumetric MR image (40), referred to as volumetric MR image (50). Next, the volumetric MR image (40) is added element-wise with the volumetric MR image (50), generating a new volumetric MR image (60).

The sixth step consists in multiplying the PET image (30) element-wise with the image of the region of interest ROI, generating a new PET image (40), as is shown in FIG. 2; and then copying the PET image (40) and inverting it on the X-axis, generating a mirror image of the PET image (40), referred to as PET image (50). Next, the PET image (40) is added element-wise with the PET image (50), generating a new PET image (60).

The seventh step corresponds to calculating a second transformation matrix M2, necessary for deforming the volumetric MR image (60) to the MR image (20); the image obtained is referred to as MR (70).

In the eighth step, the transformation matrix M2 is applied to the PET image (60), obtaining the PET image (70), which contains all the metabolic information of the patient's healthy hemisphere in the PET image (40), adding element-wise to the PET image (50) in the space of the volumetric MR image (20), which is shown in FIG. 2. In this way, the PET image (70) of the patient can be annexed to a database of virtually healthy brains.

The ninth step corresponds to calculating a third transformation matrix M3, necessary for spatially deforming the volumetric MR image (30) to the volumetric MR image (60); this transformation matrix M3 is used, later on, to obtain the image of the patient's brain metabolism in the same space as the volumetric MR image (60) and the PET image (60), as shown in FIG. 3.

In the tenth step, the transformation matrix M3 is applied to the PET image (30) obtaining the PET image (80), and subsequently the transformation matrix M2 is applied to the PET image (80) and a new PET image (90) is obtained. The PET image (90) contains all the metabolic information of the PET image (10), but now in the space of the volumetric MR image (70), which makes it possible to perform the comparative tests between the metabolic PET image of the patient (90) and a database generated with the PET images (70).

In the PET image (80) the lesion space also varied according to M3, so that a lesion (13) was generated; and similarly, in the PET image (90) the lesion space varied according to M2, so that a lesion (14) was generated, as shown in FIG. 4.

Upon completing all the described steps, the images originating from different patients exist in the same space, all with a normal metabolic pattern, offering the possibility to build a population database of PET images that enables the quantitative study thereof and thus to offer a new tool for the study of brain metabolism.

To obtain the statistical result in the PET image (20), i.e. in the patient space, the inverse matrices of M2, M3 and M1 are calculated and applied in this order to the image resulting from the comparison between the PET image (90) and the database built from the PET images (70).

The transformation matrices M1, M2 and M3 can be calculated using different approximations—linear, non-linear or combinations thereof—or carrying out another approximation that makes it possible to deform volumetric images or images acquired in 3D mode. In order to calculate the matrices M1, M2 and M3, the images with the most shape, contour and edge information are used so that the result is as accurate as possible. These usually correspond to images T1 or T2, but can also be structural images based on other parameters such as proton density images or others.

The invention claimed is:

1. A method for processing brain images, wherein the method comprises the steps of:
   a) Performing a co-registration, comprising a linear co-registration with 6 degrees of freedom for a first PET (Positron Emission Tomography) image of a patient, using as reference being a first volumetric MR (Magnetic Resonance) image of the patient, acquired in 3D mode, generating a second PET image, i.e. having identical spatial properties to the first volumetric MR image, but containing information on a patient's brain metabolism obtained in the first PET image;
   b) Calculating a first spatial transformation matrix M1, necessary for deforming the first volumetric MR image acquired in 3D mode, bringing it to the shape of a volumetric MR template image, which is an image acquired in 3D mode comprising a MR symmetric template, thus generating a second volumetric MR image which has a particularity that an interhemispheric groove coincides entirely with a coordinate value X=0;
   c) Applying the first spatial transformation matrix M1, obtained in the preceding step, to the second PET image, generating a third PET image, having identical spatial properties to the second volumetric MR image, but containing the information comprising a first lesion region on the patient's brain metabolism obtained in the first PET image;
   d) Determining a healthy hemisphere from the second volumetric MR image using information obtained from an electroencephalographic pattern or another technique to identify a laterality of patient's lesion, and once the healthy hemisphere has been identified, generating an image from dimensions of the second volumetric MR image, wherein coordinate values on the X-axis corresponding to the healthy hemisphere are 1, and the coordinate values on the X-axis of the injured side are 0, and the generated image is referred to as a region of interest ROI;
   e) Multiplying the second volumetric MR image element-wise with the generated image of the region of interest ROI, obtaining a third volumetric MR image, which corresponds only to the healthy hemisphere; copying the third volumetric MR image and inverting it on the X-axis, generating a mirror image of the third volumetric MR image, referred to as fourth volumetric MR image; and adding the third volumetric MR image element-wise with the fourth volumetric MR image, generating a fifth volumetric MR image;
   f) Multiplying the third PET image element-wise with the generated image of the region of interest ROI, generating a fourth PET image; copying the fourth PET image and inverting it on the X-axis, generating a mirror image of the fourth PET image, referred to as fifth PET image; and adding the fourth PET image element-wise with the fifth PET image, generating a sixth PET image;
   g) Calculating a second transformation matrix M2, necessary for deforming the fifth volumetric MR image to the volumetric MR template image to obtain a sixth volumetric MR image;
   h) Applying the transformation matrix M2 to the sixth PET image, obtaining the seventh PET image, which contains all the metabolic information of the patient's healthy hemisphere in the fourth PET image, adding element-wise to the fifth PET image in the space of the volumetric MR template image;
   i) Calculating a third transformation matrix M3, necessary for spatially deforming the second volumetric MR image to the fifth volumetric MR image; and
   j) Applying the transformation matrix M3 to the third PET image, obtaining the eighth PET image, and applying the transformation matrix M2 to the eighth PET image, obtaining a ninth PET image.

2. The method for processing brain images according to claim 1, wherein the first lesion region is shown in the first volumetric MR image and in the first PET image.

3. The method for processing brain images according to claim 1, wherein the transformation matrix resulting in the generation of the second volumetric MR image is referred to as matrix M1.

4. The method for processing brain images according to claim 1, wherein the first lesion region after applying the step c results in a second lesion for the second volumetric MR image and in the third PET image.

5. The method for processing brain images according to claim 1, wherein the seventh PET image of the patient is annexed to a database of virtually healthy brains.

6. The method for processing brain images according to claim 1, wherein step i) comprises using the transformation matrix M3 to obtain the image of the patient's brain metabolism in the same space as the fifth volumetric MR image and the sixth PET image.

7. The method for processing brain images according to claim 1, wherein the ninth PET image obtained contains all the metabolic information of the first PET image, but now in the space of the sixth volumetric MR image, which makes it possible to perform comparative tests between the metabolic image of the patient ninth PET image and a database generated with the seventh PET images.

8. The method for processing brain images according to claim 1, wherein the eighth PET image a third lesion space also varies according to M3, so that a third lesion is generated, and similarly, in the ninth PET image, a fourth lesion space varies according to M2, so that a fourth lesion is generated.

9. The method for processing brain images according to claim 1, further comprises calculating the inverse matrices of M2, M3 and M1, and applying them in this order to the image resulting from the comparison between the ninth PET image and the database built from the seventh PET images, in order to obtain the statistical result in the second PET image, i.e. in the patient space.

10. The method for processing brain images according to claim 1, wherein the transformation matrices M1, M2 and M3 are calculated using different approximations or carrying out another approximation to deform volumetric images or images acquired in 3D mode; and the images with the most shape, contour and edge information are used to achieve accurate corresponding images T1 or T2 as well as structural images based on other parameters comprising proton density images or others.

11. The method for processing brain images according to claim 1, wherein the brain images refer to images acquired by Positron Emission Tomography are applicable to Single-Photon Emission Computer Tomography or another technique for generating images of brain metabolism, function or blood flow.

* * * * *